United States Patent
Yu (10) Patent No.: US 8,106,151 B2
(45) Date of Patent: *Jan. 31, 2012

(54) POLYQUATERNIUM-1 SYNTHESIS METHODS

(75) Inventor: Zhi-Jian Yu, Irvine, CA (US)

(73) Assignee: Abbot Medical Optics Inc., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/693,261

(22) Filed: Jan. 25, 2010

(65) Prior Publication Data

US 2011/0027214 A1   Feb. 3, 2011

Related U.S. Application Data (63) Continuation of application No. 11/609,422, filed on Apr. 17, 2007, now Pat. No. 7,705,112.

(51) Int. Cl.
C08G 67/00 (2006.01)
C08F 14/14 (2006.01)
A61K 31/785 (2006.01)

(52) U.S. Cl. .............. 528/392; 424/78.04; 514/642
(58) Field of Classification Search .......... 528/392; 424/78.04; 514/642
See application file for complete search history.

(56) References Cited

U.S. PATENT DOCUMENTS

| | | | |
|---|---|---|---|
| 3,874,870 A | 4/1975 | Green et al. | |
| 3,931,319 A | 1/1976 | Green et al. | |
| 4,016,128 A | 4/1977 | Serlin et al. | |
| 4,027,020 A | 5/1977 | Green et al. | |
| 4,525,346 A * | 6/1985 | Stark | 424/78.04 |
| 4,734,277 A | 3/1988 | Login | |
| 4,758,595 A | 7/1988 | Ogunbiyi et al. | |
| 5,512,597 A * | 4/1996 | Kyba et al. | 514/642 |
| 5,575,993 A | 11/1996 | Ward et al. | |
| 5,603,929 A * | 2/1997 | Desai et al. | 424/78.04 |
| 6,051,611 A * | 4/2000 | Kyba et al. | 514/642 |
| 6,528,048 B1 | 3/2003 | Koike et al. | |
| 7,705,112 B2 * | 4/2010 | Yu | 528/392 |
| 7,795,374 B2 * | 9/2010 | Yu | 528/392 |

FOREIGN PATENT DOCUMENTS

GB    536017 A * 8/1941

OTHER PUBLICATIONS

Registry entry for polyquaternium-1.*
International Search Report for Application No. PCT/US08/060496, mailed on Jul. 16, 2008, 2 pages.

* cited by examiner

*Primary Examiner* — Milton I Cano
*Assistant Examiner* — Brieann R Fink (57) ABSTRACT

A ophthalmic composition, comprising:
an aqueous liquid medium, and
an effective amount of polyquaternium-1 made by a process of:
a) mixing 1,4-bis-dimethylamino-2-butene, triethanolamine and an acid;
b) introducing a 1,4-dichloro-2-butene to the mixture, and
c) isolating polyquaternium-1 having a molecular weight as determined by a proton NMR method of about 10,000 or more, at a yield of at least about 50%.

12 Claims, 9 Drawing Sheets

POLYQUATERNIUM-1 SYNTHESIS METHODS

This application is a Continuation of Ser. No. 11/609,422, filed Apr. 17, 2007, now U.S. Pat. No. 7,705,112, which is incorporated herein in its entirety.

BACKGROUND OF THE INVENTION

1. Field of the Invention

The present embodiments relate to novel synthesis methods for polyquaternium-1 and related molecules.

2. Description of the Related Art

Quaternary ammonium polymers in which the ammonium moieties are part of the linear polymeric chains have been used as antimicrobial agents in several industries. Polyquaternium-1 (PQ1) is a polymeric quaternary ammonium antimicrobial agent that has been used, for example, in preserving ophthalmic compositions and disinfecting contact lenses. PQ1 is effective against bacteria, algae and fungi.

U.S. Pat. No. 3,931,319, which is hereby incorporated in its entirety by reference, describes a two-step method for PQ1 synthesis which requires a high reaction temperature. This leads to significant degradation of the target molecule into impurities from which the desired PQ1 is difficult to separate.

U.S. Pat. No. 4,027,020, which is hereby incorporated in its entirety by reference, describes a procedure for polyquaternium-1 synthesis which results in less degradation of the resulting PQ1 than the method described in U.S. Pat. No. 3,931,319 but still produces a rather low yield. The procedure disclosed in U.S. Pat. No. 4,027,020 entails mixing 1,4-bis-dimethylamino-2-butene with triethanolamine (TEA), the molar ratio of the 1,4-bis-dimethylamino-2-butene to the TEA amine being from 2:1 to 30:1 followed by the addition of 1,4-dichloro-butene to the mixture in a molar amount equal to the sum of the molar amount of the 1,4-bis-dimethylamino-2-butene plus one-half the molar amount of TEA. The reaction time is 1-10 hours.

A major weakness of the method taught in U.S. Pat. No. 4,027,020 is that the TEA end-capping efficiency is low. As such, the final product contains a significant amount of polymers with no end caps or polymers end-capped with groups other than TEA. These malformed polymers are difficult to separate from polyquaternium-1 because of the similarity in the main chain of the polymeric molecules. Degraded or malformed polymers of PQ1 have reduced anti-bacterial efficacy and cannot substitute for PQ1 in clinical use.

SUMMARY OF THE INVENTION

Some embodiments relate to a method of making one or more quaternary ammonium polymers comprising the steps of:

a) mixing 1,4-bis-dimethylamino-2-butene, triethanolamine and an acid; and b) introducing a 1,4-dihalo-2-butene to the mixture so as to initiate a reaction resulting in the quaternary ammonium polymer.

In some embodiments, the 1,4-dihalo-2-butene is 1,4-dichloro-2-butene.

In some embodiments the quaternary ammonium polymers comprise Polyquaternium-1.

In some embodiments the acid is selected from the group consisting of HCL, $H_2SO_4$ and $H_3PO_4$.

In some embodiments the acid is HCL.

Some embodiments further comprise the step of adding water to the mixture.

In some embodiments the 1,4-bis-dimethylamino-2-butene, triethanolamine and acid are mixed before the addition of the 1,4-dihalo-2-butene.

In some embodiments the 1,4-dihalo-2-butene is added drop-wise.

In some embodiments the molar ratio of 1,4-bis-dimethylamino-2-butene to triethanolamine is from about 10:1 to about 1:5.

In some embodiments the molar ratio of triethanolamine to acid is from about 10:1 to about 1:10.

In some embodiments the molar ratio of 1,4-bis-dimethylamino-2-butene to triethanolamine to acid is from about 10:9:5 to about 10:9:8

In some embodiments the reaction temperature is from about 10° C. to about 90° C.

In some embodiments the reaction time is from about 1 hour to about 40 hours.

Some embodiments relate to a method of making Polyquaternium-1 at a yield of at least about 50% comprising the steps of:

a) mixing 1,4-bis-dimethylamino-2-butene, triethanolamine and an acid; and b) introducing a 1,4-dihalo-2-butene to the mixture so as to initiate a reaction.

In some embodiments the acid is selected from the group consisting of HCL, $H_2SO_4$ and $H_3PO_4$.

In some embodiments the 1,4-dihalo-2-butene is 1,4-dichloro-2-butene.

In some embodiments the acid is HCL.

Some embodiments further comprise the step of introducing water into the mixture.

In some embodiments the 1,4-bis-dimethylamino-2-butene, triethanolamine and acid are mixed before the addition of the 1,4-dichloro-2-butene.

In some embodiments the 1,4-dichloro-2-butene is added drop-wise.

In some embodiments the molar ratio of 1,4-bis-dimethylamino-2-butene to triethanolamine is from about 10:1 to about 1:5.

In some embodiments the molar ratio of triethanolamine to acid is from about 10:1 to about 1:10.

In some embodiments the molar ratio of 1,4-bis-dimethylamino-2-butene to triethanolamine to acid is from about 10:9:5 to about 10:9:8

In some embodiments the reaction temperature is from about 10° C. to about 90° C.

In some embodiments the reaction time is from about 1 hour to about 40 hours.

DETAILED DESCRIPTION

The present embodiments relate to methods for the synthesis of quaternary ammonium polymers. Some embodiments relate to methods for the synthesis of PQ1. Some methods involve the addition of acids to the reaction admixture to prevent impurity generation and the degradation of the synthetic quaternary ammonium polymers, including PQ1 during the synthesis of the compounds. Recent experiments have shown that past methods of synthesis of quaternary ammonium polymers as described above are not as efficient as originally thought. This is due in party to the fact that too little TEA is used in the reaction admixture.

Without intending to be bound by the structures shown, in some embodiments, PQ1 can be synthesized by the following reaction:

Some embodiments relate to a method of synthesizing PQ1 which includes the addition of acid to the admixture. Regardless of the molar ratio of TEA used, PQ1 synthesized with the methods described in U.S. Pat. Nos. 4,027,020 and 3,931,319 invariably results in significant PQ1 degradation during the reaction process. The molecular structure of PQ1 can be expressed as:

The majority of the degraded molecules are:
A) $(HOC_2H_4)_3NCH_2CH=CHCH_2(N(CH_3)_2CH_2CH=CHCH_2)_{n-1}N(CH_3)_2$ and
B) $H_2C=CHCH=CH(N(CH_3)_2CH_2CH=CHCH_2)mN(HOC_2H_4OH)_3$.

These degraded molecules are very difficult to separate from PQ1 since both are polymeric quaternary amine-based like PQ1. Degraded or malformed polymers of PQ1 have reduced anti-bacterial efficacy and cannot be substituted for PQ1 in clinical use.

It is known in the literature that $(HOC2H4)3NH+$ is not a nucleophilic agent and does not normally react with ClCH2CH=CHCH2(N(CH3)2CH2CH=CHCH2)n–1N(CH3)2CH2CH=CHCH2Cl in the end-capping step of the reaction to form PQ1. Therefore, the current literature view is that acids should be avoided in the nucleophic reaction of the present embodiments for fear that acid could convert the nucleophilic agent (HOC2H4)3N into inactive (HOC2H4)3NH+ ions. However, contrary to the current literature view, the present embodiments relate to a synthesis wherein the addition of acid to the reaction mixture does not prevent the TEA end-capping reaction.

In the methods of the prior art that do not include the addition of acid to the reaction mixture, when 1,4-bis-dimethylamino-2-butene, triethanolamine and water are mixed, the hydroxide concentration is very high, usually greater than about $10^{-3}$ M. Since the nucleophilicity of hydroxide is much stronger than that of TEA and 1,4-bis-dimethylamino-2-butene, large amounts of 1,4-dihalo-2-butene are attacked by hydroxide in the prior art methods, resulting in $HOCH_2CH=CHCH_2Cl$ or $HOCH_2CH=CHCH_2OH$. As discussed below, hydroxide also competes with TEA in the end-capping reaction of PQ1, resulting low yield and high impurities for PQ1. Therefore, in the present embodiments the presence of acid is advantageous in the reaction admixture to prevent PQ1 degradation, improve the reaction yield and reduce product impurity, regardless of the molar ratio of 1,4-bis-dimethylamino-2-butene to triethanolamine.

In some embodiments, significant PQ1 degradation during the synthesis process can be prevented by adding acid to the reaction admixture. As shown in the Examples and figures below, addition of acid greatly reduces the formation of degraded impurities and increases the yield of PQ1 in the reaction.

Some embodiments relate to a synthesis method of PQ1 involving 1,4-dihalo-2-butene. The 1,4-dihalo-2-butene can be, for example, 1,4-dichloro-2-butene, 1,4-difluoro-2-butene, 1,4-dibromo-2-butene, 1,4-diiodo-2-butene. In a preferred embodiment, the 1,4-dihalo-2-butene is 1,4-dichloro-2-butene.

The following examples are provided for illustrative purposes only, and are in no way intended to limit the scope of the present invention.

COMPARATIVE EXAMPLE 1

PQ1 was synthesized as described in U.S. Pat. No. 4,027,020 using a reactant admixture of 1,4-bis-dimethylamino-2-butene with TEA in which the molar ratio of 1,4-bis-dimethylamino-2-butene to TEA was about 5:1 and the molar ratio of 1,4-dichloro-butene to 1,4-bis-dimethylamino-2-butene was about 1.1:1. The reaction was carried out at 65° C. The proton NMR spectra were obtained for the final product after it was purified with ultrafiltration. The results are summarized in Table 1, where the peaks at the chemical shift of 6.5 ppm and 3.7 ppm are for vinyl protons in repeating units and allylic protons adjacent to the nitrogen in the ending group of the PQ1 molecules, respectively.

Table 1 one shows that the TEA end-capping efficiency is low in 6 hours reaction at which the reaction was believed by the authors of the U.S. Pat. No. 4,027,020 to be complete. The reaction time was then extended from 6 to 10 hours and the results show that the amount of proton in the end cap group of the polymers is still increasing. Therefore, the end-capping reaction for PQ1 synthesis is not completed at 6 hours and is approximately only 71% complete.

TABLE 1

| Reaction Time | Peak area at 6.5 ppm Chemical shift | Peak area at 3.7 ppm Chemical shift |
|---|---|---|
| 6 hours | 1.000 | 0.0343 |
| 10 hours | 1.000 | 0.0481 |

The low end-capping efficiency is due to the low amount of TEA in the reactant admixture. The low TEA concentration in the reaction mixture slow down its kinetic reaction rate with $ClCH_2CH=CHCH_2(N(CH_3)_2CH_2CH=CHCH_2)_n$ $CH_2CH=CHCH_2Cl$. Meanwhile, water molecules and hydroxide ions (OH—) in the solution may compete with TEA to form $OHCH_2CH=CHCH_2(N(CH_3)_2CH_2CH=CHCH_2)_nCH_2CH=CHCH_2OH$.

Figure 1A:
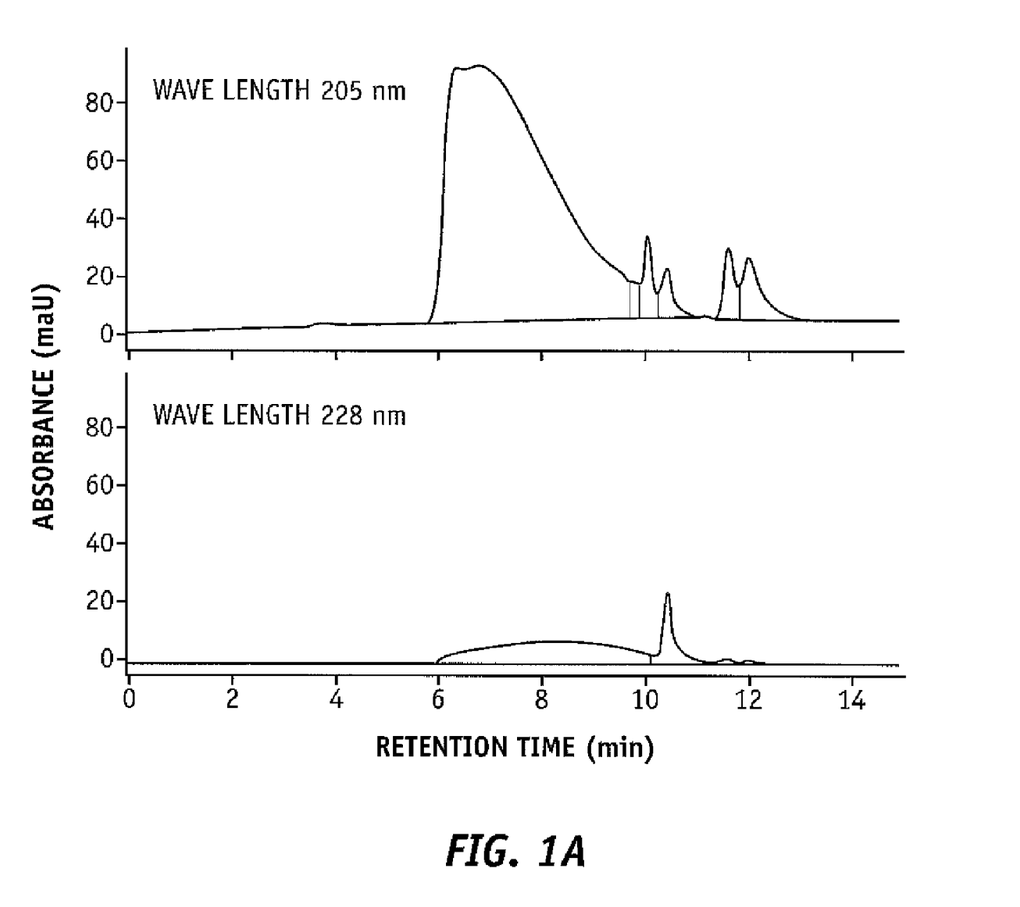
FIG. 1 shows GPC chromatograms for the products of the reaction as described below in comparative example 1 with no acid added to the reaction mixture.
Figure 1B:
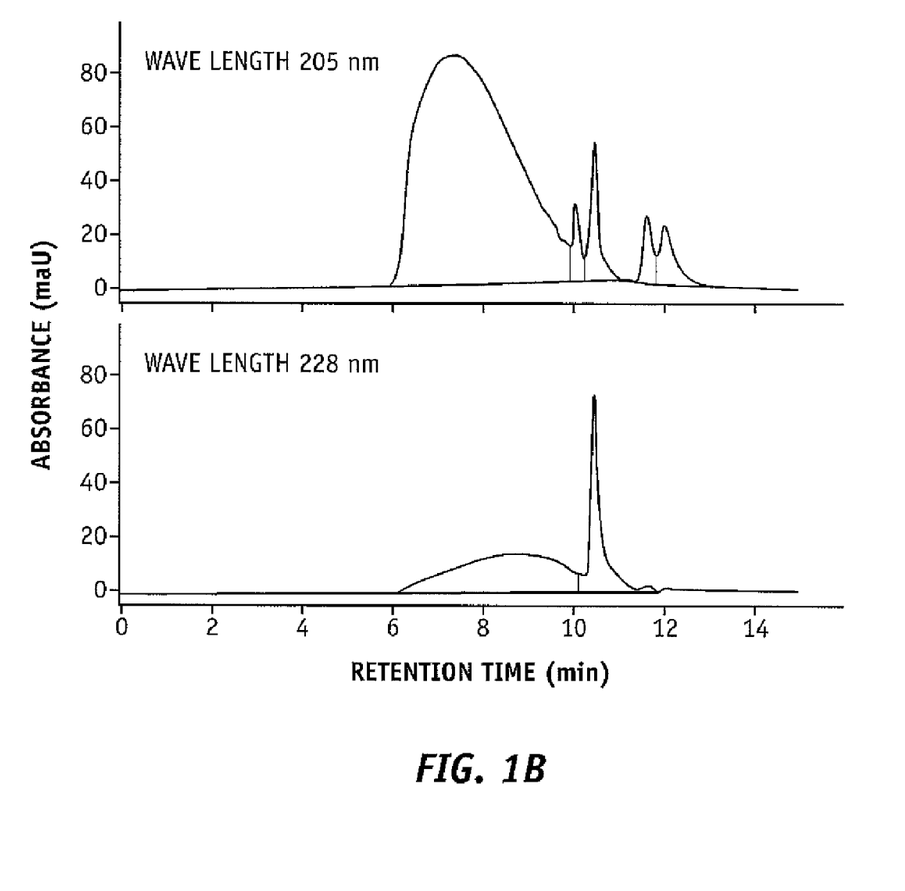
Figure 1C:
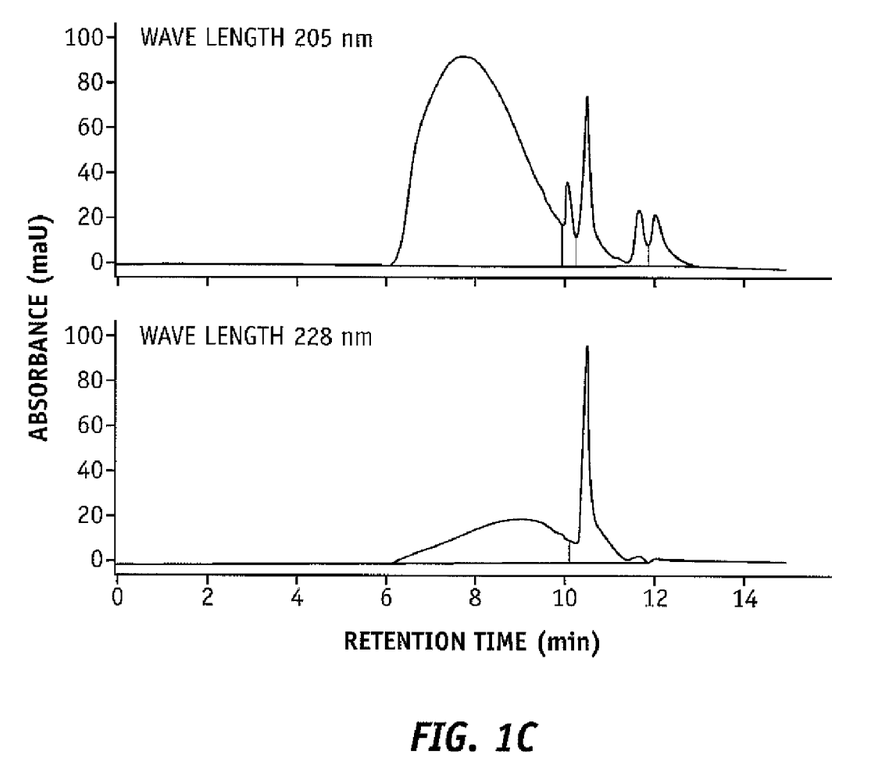

FIGS. 1a, 1b and 1c represent the GPC chromatograms for PQ1 synthesized with admixtures of 1 mole of 1,4-bis-dimethylamino-2-butene, 0.9 moles of TEA, and 1.15 moles of 1,4-dichlo-butene at 65° C. at 2, 6 and 10 hours respectively. A GPC-HPLC chromatograph was used to trace the PQ1 molecular size. The experimental conditions were: an aqueous solution of 0.045 M $KH_2PO_4$, 0.45% NaCl and 9.1% $CH_3CN$ as a mobile phase in a Phenomenex BioSep-SEC-S 2000 column and an Agilent 1100 Series HPLC system equipped with PDA detector. PQ1 molecules have an absorbance peak at 205 nm but do not have an absorbance peak at 228 nm. However, the degraded molecules have an absorbance maximum at 228 nm. Therefore the detection wavelengths of 205 nm and 228 nm are used to trace PQ1 and its degradated segments, respectively, during the reaction process.

The broad peak shown in FIGS. 1a, 1b and 1c which ranges from 6 to 10 minutes retention time represents polymeric molecules of PQ1 and its degraded products. The larger the polymeric molecules, the shorter the retention time will be. The water solvent peak locates at about 10 minutes. The peaks beyond 10 minutes represent non-polymeric small molecules of either the reactants or bi-products.

Figure 2:
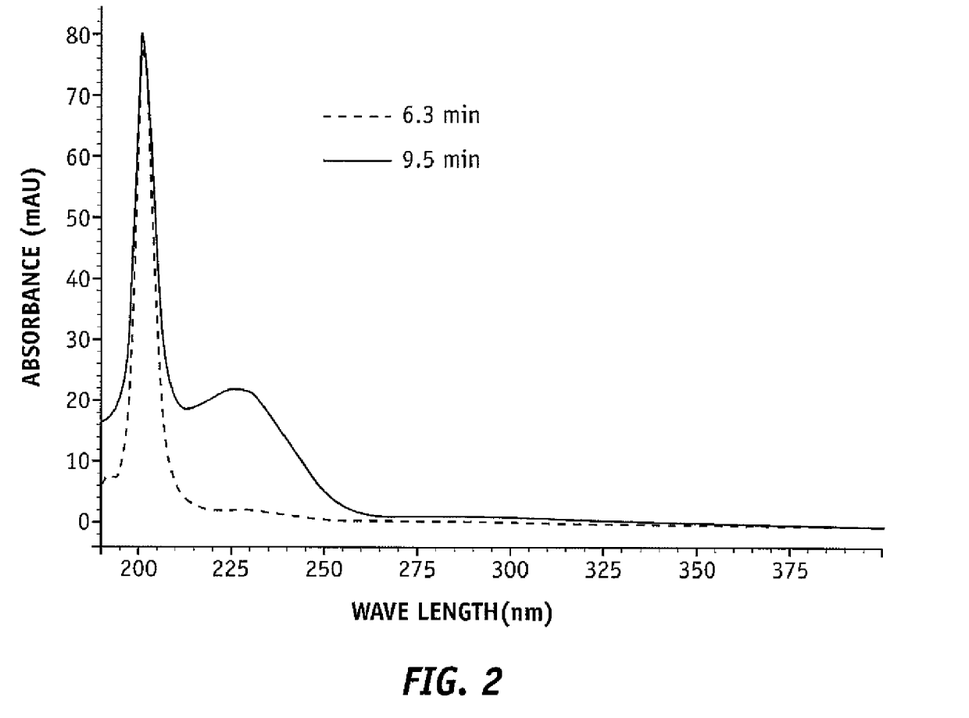
FIG. 2 shows the spectrum of the large PQ1 molecules at retention time of 6.3 minutes and at 9.5 minutes of the products of the reaction as described below in comparative example 1 without acid added.

As can be seen in FIG. 2, the crude PQ1 product synthesized as described in the U.S. Pat. No. 4,027,020 without adding acid shows absorbance at 228 nm. The absorbance peak shifts to a longer retention time with increase of reaction time from 8.4 min at 2 hours (see FIG. 1a) to 9 minutes at 10 hours (see FIG. 1c). FIG. 2 further shows that the spectrum of the large PQ1 molecules at retention time of 6.3 minutes has no absorbance at 228 nm and that the spectrum at 9.5 minutes possess a strong absorbance at 228 nm. Clearly, there are two or more types of different polymeric quaternary amines generated in the product mixture. The large polymers are close to PQ1 and the small polymers correspond to the degraded PQ1.

In the present embodiments, any acid can be used in the synthetic method. In preferred embodiments, the acid used does not contain a strong nucleophilic group. Preferred acids include HCl, $H_2SO_4$, and $H_3PO_4$ but the present embodiments are not limited to these acids. Additional suitable acids include acetic acid, succinic acid, and citric acid, among others.

COMPARATIVE EXAMPLE 2

Figure 5:
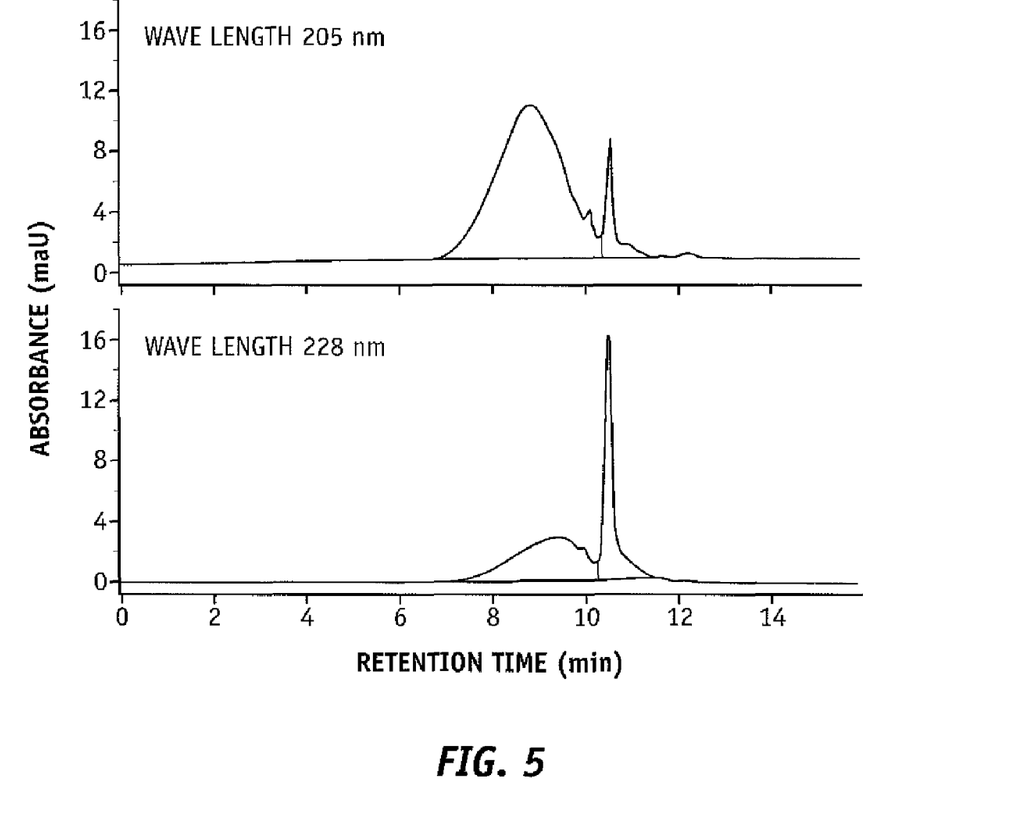
FIG. 5 shows the GPC chromatograms for the products of the reaction as described in comparative example 2.

FIG. 5 shows the GPC chromatograms for the products of the reaction as described above in Comparative Example 1 except with a specific reaction admixture of 1 mole of 1,4-bis-dimethylamino-2-butene, 1.2 moles of TEA, and 1.2 moles of 1,4-dichlo-butene at 60° C. for 18 hours. No acid was added to the reaction admixture.

The severe degradation during synthesis process is shown with strong absorption at 228 nm. The long retention time also indicates that PQ1 was degraded into smaller molecular size. Another indication of PQ1 degradation in the absence of acid is the increase of peak area at the retention time of 10.5 minutes over reaction time from FIGS. 1 and 5. This peak corresponds to non-polymeric small molecules with similar absorbance spectrum maximum at 225 nm as that of 228 nm for one of the degraded PQ1 molecules. It is likely that all PQ1 will eventually be degraded in to the small molecules during reaction or storage if the time is long enough.

COMPARATIVE EXAMPLE 3

In order to prevent the side end-capping reaction and increase the main end-capping, reaction rate, the amount of TEA in the admixture of the reactants was increased. Table 2 shows the proton NMR spectrum data for PQ1 synthesized at 65° C. with admixture of 1 mole of 1,4-bis-dimethylamino-2-butene, 0.9 moles of TEA, and 1.15 moles of 1,4-dichlo-butene (the molar ratio of 1,4-bis-dimethylamino-2-butene with TEA is 1.11:1 instead of 5:1 as in Example 1 above). The far right column of Table 2 lists the end-capping percentage over the reaction time. It can be seen that even at the presence of large excess amount of TEA, the reaction is still not complete until a time of 4 hours. See FIGS. 1 and 2.

TABLE 2

| Reaction Time | Peak area at 6.5 ppm Chemical shift | Peak area at 3.7 ppm Chemical shift | End-capping efficiency |
|---|---|---|---|
| 2 hours | 1.000 | 0.108 | 94.7% |
| 4 hours | 1.000 | 0.114 | 100% |
| 6 hours | 1.000 | 0.114 | 100% |

EXAMPLE 1

10.14 grams (71.3 mmoles) of 1,4-bis-dimethylamino-2-butene, 6.4 grams (42.8 mmoles) of TEA, 4.92 ml of 6N HCl (29.5 mmoles), 18.8 grams of water and a stir bar were combined in a 100 ml three-mouth flask. The flask was submerged into an ice water bath. 9.8 grams of (78.4 mmoles) of 1,4-dichloro-2-butene were slowly added drop-wise into the flask under constant stirring. The ice-bath was removed after the 1,4-dichloro-2-butene was completely added and the flask was submerged in a warm-water bath (25-40° C.) for 20 minutes. The water bath was heated until the temperature inside the flask reached 70° C. The reaction was stopped after 21 hours by removing the flask from the water bath. Variations can be made to the procedure by those skilled in the art for larger scale production to release the heat generated at the initial stage of the reaction before raising the temperature to above 60° C.

Figure 3A:
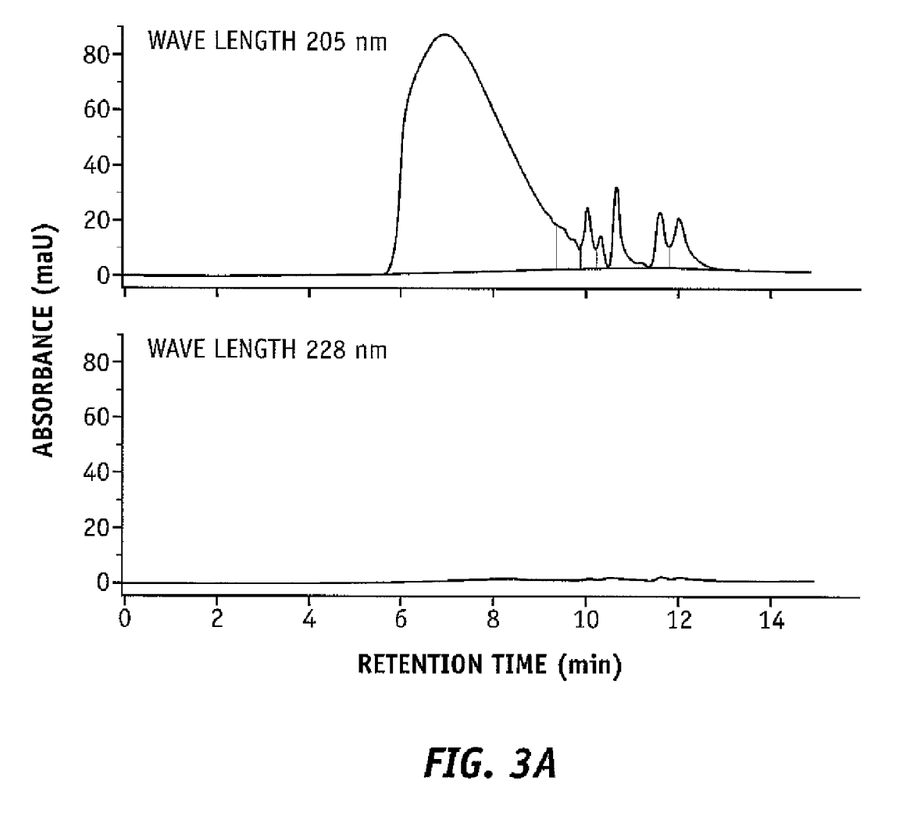
FIG. 3 shows the GPC chromatograms for the products of the reaction as described in example 1 with acid added.
Figure 3B:
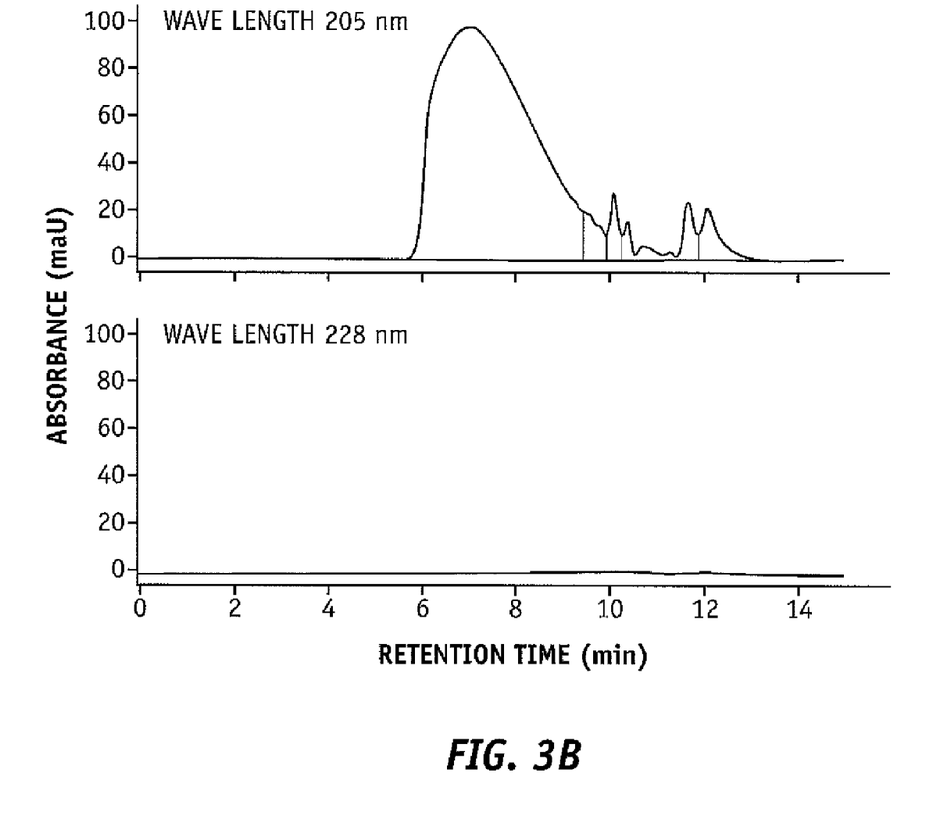
Figure 3C:
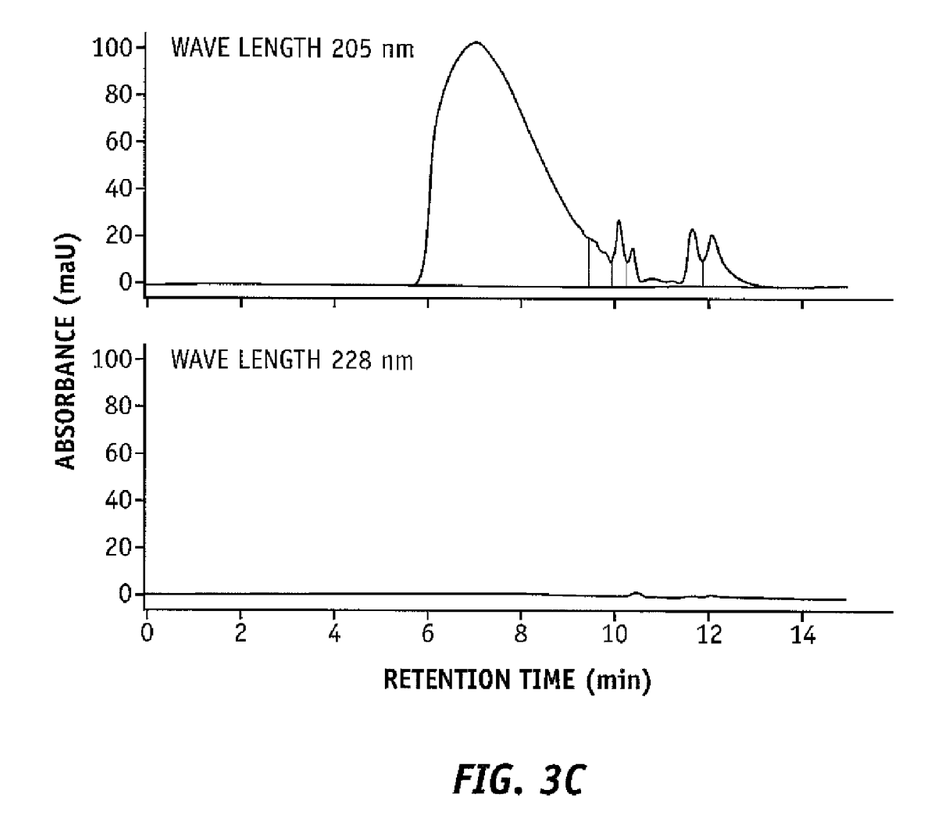
Figure 4:
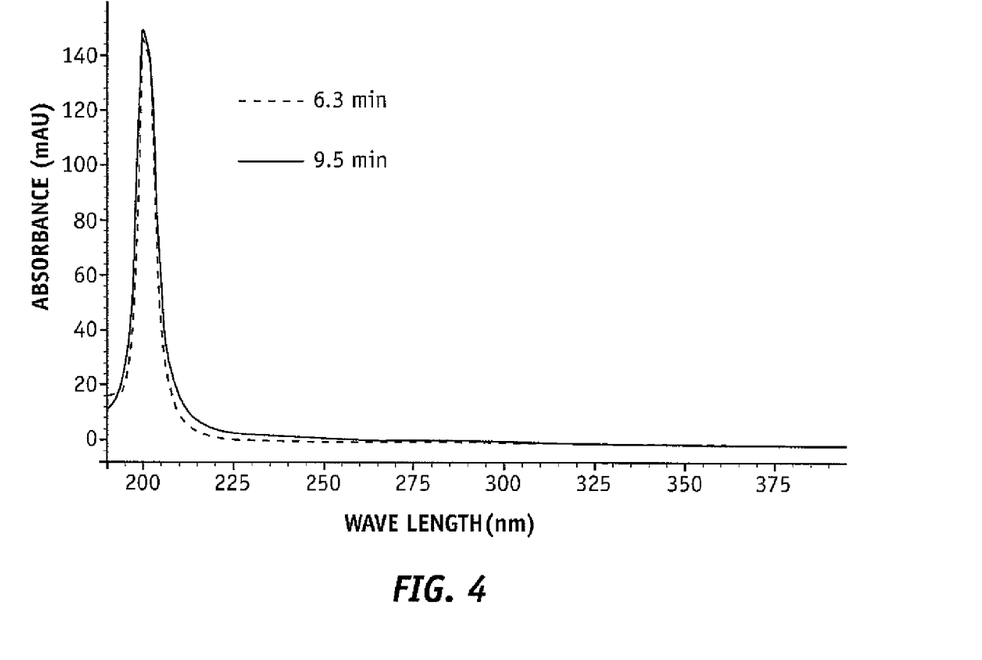
FIG. 4 shows 4 the spectra of the synthesized crude product at 6 hours reaction time at 6.3 and 9.5 minutes retention time, respectively of the products of the reaction described in example 1 with acid added.

FIGS. 3a, 3b and 3c are the GPC chromatograms for the above admixtures with HCl added. The peak at 205 nm in each chromatogram shows the presence of PQ1, while the lack of peak at 228 nm indicates the absence of degradation products. FIG. 4 is the spectra of the synthesized crude product at 6 hours reaction time at 6.3 and 9.5 minutes retention time, respectively. It can be seen that there is no absorbance at 228 nm in the whole 10 hours reaction period when the acid is added to the reaction mixture, indicating that no degraded PQ1 has been formed. FIG. 4 further confirms that there is no absorbance peak at 228 nm at the whole retention time range of 6-10 minutes. This result indicates that the addition of the acid effectively prevented the formation of degraded PQ1.

TABLE 3

Summary of Peak Retention Time for the Products Synthesized with and without Acid

| Reaction | Peak retention time without acid | | Peak retention time with acid | |
| --- | --- | --- | --- | --- |
| Time | 205 nm | 228 nm | 205 nm | 228 nm |
| 2 hours | 6.7 | 8.4 | 6.9 | no peak |
| 6 hours | 7.3 | 8.9 | 6.9 | no peak |
| 10 hours | 7.6 | 9.0 | 6.9 | no peak |

The absorbance at 205 nm is mainly from the molecule back-bone structure. Table 3 further shows that the polymer molecular size distribution measured at 205 nm is stable in the system where the acid is added.

As one of ordinary skill in the art will appreciate, the above crude PQ1 products can be purified by removing the excess amount of TEA, the acid, 1,4-dichloro-2-butene and other small molecule byproduct/impurities which are shown up at the retention time of >10 minutes in FIGS. 1 and 3 using methanol and/or acetone as solvents.

EXAMPLE 2

Polyquaternium-1 Synthesis Procedure for Sample #2 in Table 4

10.14 grams (71.3 mmoles) of 1,4-bis-dimethylamino-2-butene, 6.4 grams (42.8 mmoles) of TEA, 4.92 ml of 6N HCl (29.5 mmoles), 18.8 grams of water and a stir bar were combined in a 100 ml three-mouth flask. The flask was then submerged into an ice water bath. 9.8 grams (78.4 mmoles) of 1,4-dichloro-2-butene were added (drop-wise) into the flask under constant stirring. The ice-bath was removed after all of the 1,4-dichloro-2-butene was completely added and the flask was submerged into a warm-water bath (25-40° C.) for 20 minutes. The water bath was heated until the temperature in the flask reached 70° C. The reaction was stopped after 21 hours by removing the flask from the water bath.

Table 4 lists PQ1 synthesized with addition of acid to the reaction mixture. Each sample was prepared as described above for Sample #2 except with different molar ratios of reactants. No absorbance was observed at 228 nm, i.e., no degradation of PQ1 occurred for any of the samples. The molecular weight was measured by the proton NMR method.

TABLE 4

| Sample # | Molar ratio | | Reaction Time | Reaction Temperature | PQ1 Molecular weight |
| --- | --- | --- | --- | --- | --- |
| | DA*/TEA | DA/DCB*/HCl | | | |
| 1 | 0.83 | 1/1.2/0.83 | 5 hours | 70° C. | 6.94k |
| 2 | 1.67 | 1/1.1/0.41 | 21 hours | 70° C. | 11.4k |
| 3 | 1.25 | 1/1.1/0.55 | 8 hours | 75° C. | 9.3k |
| 4 | 0.83 | 1/1.2/0.83 | 8 hours | 60° C. | 7.7k |
| 5 | 1.11 | 1/1.15/0.62 | 6 hours | 60° C. | 10k |
| 6 | 5.0 | 1/1.1/1 | 18 hours | 75° C. | 26k |

*DA = 1,4-bis-dimethylamino-2-butene, DCB = 1,4-dichloro-butene

As described in U.S. Pat. No. 4,027,020, PQ1 synthesis without the addition of acid to the reaction mixture is not effective outside the range of DA/TEA molar ratio of 2:1-30:1. Table 4 above shows that the methods of the present embodiments are effective with a much larger ranger of DA/TEA molar ratios. In some embodiments, PQ1 can be effectively formed at DA/TEA molar ratio <2:1. In fact, the molecular size of PQ1 is related to the ratio of DA/TEA: the higher the ratio, the higher the PQ1 molecular weight.

The preferred molar ratio of the total amines (DA+TEA) to acid is from about 10:1 to about 1:2 and most preferably from about 5:1 to about 1:1. The preferred DA/TEA ratio is from about 0.3:1 to about 30:1 and most preferably from 0.8:1 to about 5:1.

The molecular weights are deduced from the proton NMR spectrum of the product according to the equation: $mw = 133.5(6u/v-1) + 290$, where u is the peak area at the chemical shift of 6.5 ppm which is from the vinyl protons in the repeating units, and v is peak area at the chemical shift of 3.7 ppm which is from the allylic protons adjacent to nitrogen in the ending groups of the PQ1 molecules.

EXAMPLE 3

An experiment was done to test the anti-bacterial effect of PQ1 synthesized in the presence of acid in comparison to PQ1 molecules synthesized without the presence of acid. Several contact lens multi-purpose solutions were formulated by dissolving the ingredients in Table 5 in deionized water. Antimicrobial activity was tested by methods known in the art against the FDA contact lens disinfection panel. Log reductions at 6 hours solution contact are reported at the bottom of Table 5.

TABLE 5

|  | % w/w % w/w % w/w PQ1 synthesized with acid added (sample# 5 in Table 4) | | | % w/w % w/w % w/w PQ1 synthesized without acid* | | |
| --- | --- | --- | --- | --- | --- | --- |
| PQ-1 | 0.000075 | 0.0001 | 0.00015 | 0.000075 | 0.0001 | 0.00015 |
| Hydroxypropylmethylcellulose (HPMC) | 0.20 | 0.20 | 0.20 | 0.20 | 0.20 | 0.20 |
| Sodium Chloride | 0.59 | 0.59 | 0.59 | 0.59 | 0.59 | 0.59 |
| Potassium Chloride | 0.14 | 0.14 | 0.14 | 0.14 | 0.14 | 0.14 |
| Tris HCl | 0.055 | 0.055 | 0.055 | 0.055 | 0.055 | 0.055 |
| Tris (base) | 0.021 | 0.021 | 0.021 | 0.021 | 0.021 | 0.021 |
| Taurine | 0.05 | 0.05 | 0.05 | 0.05 | 0.05 | 0.05 |
| Poloxamer 237 | 0.05 | 0.05 | 0.05 | 0.05 | 0.05 | 0.05 |
| Edetate Disodium | 0.01 | 0.01 | 0.01 | 0.01 | 0.01 | 0.01 |
| Propylene Glycol | 0.50 | 0.50 | 0.50 | 0.50 | 0.50 | 0.50 |
| Purified Water | 98.38 | 98.38 | 98.38 | 98.38 | 98.38 | 98.38 |
| Log drop at 6 hours | | | | | | |
| S. marcescens 13880 | 2.12 | 2.18 | 2.18 | 0.01 | 0.14 | 0.37 |
| C. albicans 10231 | 0.36 | 0.54 | 0.45 | 0.21 | 0.21 | 0.17 |
| P. aeruginosa 9027 | >5.00 | >5.00 | >5.00 | | | |
| S. aureus 6538 | 2.89 | 2.99 | 3.32 | | | |
| F. solani 36031 | 2.65 | 2.90 | 3.40 | | | |

*Synthesized according to the conditions described in Comparative Example 2 except the reaction time is 40 hours.

As can be seen in Table 5, above, the antimicrobial activity is reduced considerably when PQ1 is generated without the presence of acid; that is, when PQ1 is degraded.

EQUIVALENTS

The foregoing written specification is considered to be sufficient to enable one skilled in the art to practice the invention. The foregoing description details certain preferred embodiments of the invention and describes the best mode contemplated by the inventor. It will be appreciated, however, that no matter how detailed the foregoing may appear in text, the invention may be practiced in many ways and the invention should be construed in accordance with the appended claims and any equivalents thereof.

What is claimed is:

1. A ophthalmic composition, comprising:
   an aqueous liquid medium, and
   an effective amount of polyquaternium-1 made by a process of:
   a) mixing 1,4-bis-dimethylamino-2-butene, triethanolamine and an acid;
   b) introducing a 1,4-dichloro-2-butene to the mixture, and
   c) isolating polyquaternium-1 having a molecular weight as determined by a proton NMR method of about 10,000 or more, at a yield of at least about 50%.

2. The ophthalmic composition of claim 1, wherein the acid is selected from the group consisting of HCl, $H_2SO_4$ and $H_3PO_4$.

3. The ophthalmic composition of claim 1, wherein the acid is HCl.

4. The ophthalmic composition of claim 1, further comprising the step of introducing water into the mixture.

5. The ophthalmic composition of claim 1, wherein the 1,4-bis-dimethylamino-2-butene, triethanolamine and acid are mixed before the addition of the 1,4-dichloro-2-butene.

6. The ophthalmic composition of claim 1, wherein the 1,4-dichloro-2-butene is added drop-wise.

7. The ophthalmic composition of claim 1, wherein the molar ratio of 1,4-bis-dimethylamino-2-butene to triethanolamine is from about 10:1 to about 1:5.

8. The ophthalmic composition of claim 1, wherein the molar ratio of triethanolamine to acid is from about 10:1 to about 1:10.

9. The ophthalmic composition of claim 1, wherein the molar ratio of 1,4-bis-dimethylamino-2-butene to triethanolamine to acid is from about 10:9:5 to about 10:9:8.

10. The ophthalmic composition of claim 1, wherein the reaction temperature is from about 10° C. to about 90° C.

11. The ophthalmic composition of claim 1, wherein the reaction time is from about 1 hour to about 40 hours.

12. The ophthalmic composition of claim 1, wherein the ophthalmic composition is a multipurpose solution for contact lens care.

* * * * *

UNITED STATES PATENT AND TRADEMARK OFFICE
CERTIFICATE OF CORRECTION

PATENT NO. : 8,106,151 B2
APPLICATION NO. : 12/693261
DATED : January 31, 2012
INVENTOR(S) : Zhi-Jian Yu It is certified that error appears in the above-identified patent and that said Letters Patent is hereby corrected as shown below:

Cover Page: Item 73 should read
    Assignee: Abbott Medical Optics Inc., Santa Ana, CA (US)

Signed and Sealed this
Twenty-fourth Day of April, 2012

David J. Kappos
*Director of the United States Patent and Trademark Office*